United States Patent [19]

Thies et al.

[11] 4,209,469

[45] Jun. 24, 1980

[54] PROCESS FOR THE PRODUCTION OF ARYL THIOLS

[75] Inventors: Hans Thies, Rheinfelden, Fed. Rep. of Germany; Fred von Kaenel, Seltisberg, Switzerland

[73] Assignee: Ciba-Geigy Aktiengesellschaft, Basel, Switzerland

[21] Appl. No.: 971,135

[22] Filed: Dec. 19, 1978

[30] Foreign Application Priority Data

Dec. 30, 1977 [CH] Switzerland ............... 16300/77

[51] Int. Cl.$^2$ ............................................. C07C 148/00
[52] U.S. Cl. ........................................................ 568/68
[58] Field of Search .................................... 260/609 D

[56] References Cited

U.S. PATENT DOCUMENTS

| | | | |
|---|---|---|---|
| 2,402,641 | 6/1946 | Lazier et al. | 260/609 D |
| 3,069,472 | 12/1962 | Loev et al. | 260/609 D |
| 3,399,238 | 8/1968 | Greenfield | 260/609 D |
| 4,005,149 | 1/1977 | Kubicek | 260/609 D |
| 4,128,586 | 12/1978 | Ratcliffe | 260/609 D |

FOREIGN PATENT DOCUMENTS

| | | | |
|---|---|---|---|
| 1903968 | 8/1970 | Fed. Rep. of Germany | 260/609 D |
| 461101 | 4/1975 | U.S.S.R. | 260/609 D |

OTHER PUBLICATIONS

Houben-Weyl, Methoden der Organische Chemie, IX, pp. 29 et seq. (1952).

*Primary Examiner*—Donald G. Daus
*Assistant Examiner*—M. C. Eakin
*Attorney, Agent, or Firm*—Sprung, Felfe, Horn, Lynch & Kramer

[57] ABSTRACT

A process for the production of an aryl thiol, which comprises hydrogenating an aryl sulfochloride in a protic or aprotic solvent in the presence of platinum as catalyst, at a temperature between 100° and 180° C., with hydrogen under a pressure of 2 to 140 bar, in a single reaction step.

13 Claims, No Drawings

PROCESS FOR THE PRODUCTION OF ARYL THIOLS

The present invention provides a novel process for the production of aryl thiols by hydrogenating aryl sulfochlorides in the presence of platinum catalysts.

It is known that aryl sulfinates, aryl thiosulfonates and aryl sulfochlorides can be hydrogenated to thiophenols in the presence of sulfides or polysulfides of cobalt, nickel, iron or molybdenum at temperatures from 150° to 275° C. and pressures from 30 to 170 bar (U.S. Pat. No. 2,402,641).

USSR Pat. specification No. 461.101 describes the reduction of 2-naphthylsulfochloride with hydrogen in the presence of cobalt polysulfide at 130° to 150° C. and 50 to 100 bar in chlorobenzene. In addition, it is known from German Offenlegungsschrift 1,903,968 that diphenyl disulfide can be reduced with hydrogen at 150 bar in the presence of nickel or cobalt sulfide or nickel or cobalt polysulfide as catalyst to produce the corresponding thiophenol.

According to Netherlands patent application No. 66.11430, hydrogenation of the sodium salts of benzenesulfinic acid and p-toluenesulfinic acid in the form of an aqueous solution at temperatures between 125° and 200° C. and pressures between 30 and 105 bar, with hydrogen in the presence of platinum sulfide on carbon as catalyst, affords the corresponding thiophenols.

Furthermore, attention is drawn also to the prejudice found even in the literature (Houben-Weyl., Meth. der Org. Chemie, 4th edition, Vol. IX, pages 29 ff) regarding the subject matter of the invention, that only modest yields of thiophenols are obtained in the reduction of sulfonic acid chlorides from a suspension of iron or zinc, especially at elevated temperatures and in the presence of water (water of reaction). The disproportionation of aryl sulfinic acids as intermediate, which proceeds in accordance with the following reaction scheme, is held to be responsible for this reduction in the yield:

3 ArSO$_2$H→ArSO$_2$SAr+ArSO$_3$H+H$_2$O

5 ArSO$_2$H→Ar-S-S-Ar+3ArSO$_3$H+H$_2$O.

In contradistinction to the sulfochlorides, the sulfonic acids obtained during the disproportionation can no longer be reduced to the thiophenol. In addition, large amounts of ecologically harmful metal salts, which require reprocessing, are formed during the reaction. All the processes referred to above have, moreover, a number of drawbacks. Thus, many of these reactions proceed via a number of steps and, especially in the case of the halogenated aromatics, afford inhomogeneous products. This results in satisfactory yields and necessitates additional cleansing operations. All these difficulties have led to the search for a novel process which permits aryl thiols to be produced in simple manner and in the requisite purity and yield. Surprisingly, it has now been found that the disadvantages recited above do not occur by hydrogenating aryl sulfochlorides in organic solvents in the presence of platinum catalysts and that the corresponding aryl thiols are obtained in a high degree of purity and in high yield in a single reaction step. In particular, the reduction is not adversely affected by substituents, for example chlorine bonded to aromatics is not replaced.

The novel process for the production of aryl thiols consists in hydrogenating aryl sulfochlorides in protic or aprotic organic solvents, in the presence of platinum catalysts at temperatures between 100° and 180° C., with hydrogen under a pressure of 2 to 140 bar, in a single reaction step.

Preferably, the reaction proceeds such that a preliminary hydrogenation is carried out with 1 mole of hydrogen per mole of sulfochloride at a temperature between 20° and 50° C. and only subsequently heating the reaction mixture. The further hydrogenation is carried out between 120° and 180° C., especially between 140° and 150° C., and under a hydrogen pressure in the range from 20 to 120 bar, especially from 30 to 100 bar. The reaction course is illustrated by the following equation:

ArSO$_2$Cl+3H$_2$→ArSH+2H$_2$O+HCl.

Eligible starting compounds for the process of the invention are mononuclear and polynuclear unsubstituted and substituted aryl sulfochlorides. Examples of substituents are: halogen, in particular chlorine, alkyl groups, such as ethyl and especially methyl, alkoxy groups, such as methoxy, alkylaryl groups or aryloxy groups. Representative examples of the compounds themselves are: benzenesulfochloride, 4-chlorobenzenesulfochloride, 3-methyl-4,6-dichlorobenzenesulfochloride, 3-chloro-5-methyl-6-cyanobenzenesulfochloride, 2-naphthalenesulfochloride, 1-chloro-8-naphthalenesulfochloride and 2,5-dichlorobenzenesulfochloride.

The catalyst employed is advantageously commercially available platinum on a carrier having a high specific surface area. Such carriers are for example: activated charcoal, silica gel, alumina or magnesia. In the process of the present invention, it is advantageous to use 100 to 200 mg, in particular 200 to 400 mg, of catalyst per mole of aryl sulfochloride. Sulfidised platinum can also be used as catalysts.

Suitable solvents as reaction medium are all those solvents in which the reaction substrates and products are soluble and which are resistant to the reduction. Instead of a single solvent, it is also possible to use a solvent mixture.

Preferred solvents are lower aliphatic alcohols, such as isopropanol and ethanol, but also for example dimethyl formamide, as well as aromatic solvents, for example toluene, xylenes and chlorobenzenes. In special cases, aliphatic hydrocarbons or mixtures thereof, for example white spirit, are also suitable.

A ratio of aryl sulfochloride to solvent of 1:0.5 to 1:20 and, in particular, of 1:2 to 1:5, is advantageously used in the process of the present invention.

The single-pot process of the invention is carried out as follows: A double-jacketed pressure autoclave (maximum operating pressure 150 bar) made of Hastelloy B ® or enamelled steel and fitted with a gas absorption stirrer (approx. 1500 rpm), thermometer, pressure gauge, excess pressure valve with bursting disc, is charged with a solution of an aryl sulfochloride in a polar solvent, for example isopropanol. To this solution are added, per mole of substrate, about 4 to 8 g of catalyst (200 to 400 mg of platinum on charcoal). The internal pressure is then increased to 5 bar with hydrogen and for 20 minutes a tightness control of the reactor and the hydrogen reservoir is made.

The initial hydrogenation should be carried out with the admission valve open (hydrogen pressure of 40 bar) with 1 mole of hydrogen per mole of substrate at a temperature below 50° C. Then the reactor contents are brought to a temperature of 140° C. in the course of 60 minutes with the steam circulation and this temperature is kept for 30 minutes. The hydrogen uptake is ordinarily about 95 to 100% of theory. The contents of the reactor are then cooled to 60° C. and, after closing the admission valve, the hydrogen pressure is reduced to 1 bar by releasing it into the atmosphere. To expel hydrogen from the reactor, nitrogen is blown in at a pressure of 5 bar and the pressure is then reduced to zero. This operation is carried out 3 times. The reactor contents are then discharged through a preheated pressure filter made of Hastelloy B ® (hot water heating) into a tared transportation container and washed with isopropanol. The isopropanolic filtrate contains the product and is adjusted to a pH value of 9 to 12 with alkali lye. The main solution and the wash solution are combined and subjected to distillation. When the solvent has been more or less distilled off, the reaction product can be isolated from the residue. The product is of such purity that it can be further reacted direct without isolation. The catalyst which has been previously filtered off can be used for further reactions, if necessary after regeneration.

The products obtained by the single-step process of the invention are valuable intermediates for the production of dyes and coloured pigments, for example by reaction with chloroacetic acid to produce the corresponding thioglycolic acids.

The process of the invention is illustrated by the following Examples.

EXAMPLE 1

A 2500 cm³ capacity enamel autoclave (conventional construction of Hastelloy B ®) is charged with 245.5 g (1 mole) of 2,5-dichlorophenyl-1-sulfochloride in 1100 ml of isopropanol and 4 g of platinum on carbon catalyst (200 mg of platinum). Air is displaced by blowing in nitrogen at a pressure of 5 bar and reducing the pressure to zero. This operation is performed 3 times. Nitrogen is expelled in the same way with hydrogen. The hydrogen pressure is then adjusted to 40 bar by means of a pressure reducing valve. A tightness control of the apparatus is made and the agitator is set in motion at 1200 min⁻¹. The reaction temperature increases in the course of 1 to 2 minutes from 20° to 50° C. and falls again in the course of a further 5 minutes to 40° C. The hydrogen uptake during this time is about 1 mole. The contents of the autoclave are then heated approximately linearly to 140° C. in the course of 50 minutes and this temperature is kept for 30 minutes. After cooling, the hydrogen pressure is released into the atmosphere. The hydrogen is expelled from the autoclave by blowing in nitrogen at a pressure of 5 bar and reducing the pressure to zero. This operation is performed 3 times. The catalyst is removed by filtration and the filtrate is made alkaline by addition of 2.5 moles of approx. 30% sodium hydroxide solution (250 ml).

After distilling off the isopropanol-H$_2$O azeotrope, the resulting 2,5-dichlorothiophenolate can be reacted, without isolation, virtually quantitatively with 1.05 mole of chloroacetic acid to produce 2,5-dichlorophenyl-1-thioglycolic acid.

The total yield of 2,5-dichlorothiophenol in the course of several experiments was between 93% and 96% of theory.

EXAMPLE 2

2,5-Dichlorothiophenol was also obtained in a yield of 95% of theory by repeating the procedure of Example 1 but using 122.8 g (0.5 mole) of 2,5-dichlorophenyl-1-sulfochloride in 600 ml of toluene and 7 g of moist sulfonated platinum on carbon catalyst (40 to 50% water content, 5% dry platinum), applying a hydrogen pressure of 120 to 155 bar, heating to 150° C. and keeping this temperature for 6 hours.

EXAMPLES 3 to 12

The procedure of Example 1 is repeated using equimolar amounts of the aryl sulfochlorides listed in column 2 of the following table. The corresponding aryl thiols listed in column 3 are obtained in the same purity and also in yields of more than 90% of theory.

TABLE

| Ex. | Aryl sulfochlorides | Aryl thiols |
| --- | --- | --- |
| 3 | C$_6$H$_5$—SO$_2$Cl | thiophenol |
| 4 | 4-CH$_3$—C$_6$H$_4$—SO$_2$Cl | 4-methylthiophenol |
| 5 | 4-Cl—C$_6$H$_4$—SO$_2$Cl | 4-chlorothiophenol |
| 6 | 4-CH$_3$-3-Cl—C$_6$H$_3$—SO$_2$Cl | 4-methyl-3-chloro-thiophenol |
| 7 | 2-Cl-3,5-(CH$_3$)$_2$—C$_6$H$_2$—SO$_2$Cl | 2-chloro-3,5-dimethyl-thiophenol |
| 8 | 2,5-(CH$_3$)$_2$-4-Cl—C$_6$H$_2$—SO$_2$Cl | 2,5-dimethyl-4-chloro-thiophenol |
| 9 | 3-CH$_3$-4,6-Cl$_2$—C$_6$H$_2$—SO$_2$Cl | 3-methyl-4,6-dichloro-thiophenol |
| 10 | 3-Cl-5-CH$_3$-6-CN—C$_6$H$_2$—SO$_2$Cl | 3-chloro-5-methyl-6-cyano-thiophenol |

TABLE-continued

| Ex. | Aryl sulfochlorides | Aryl thiols |
| --- | --- | --- |
| 11 | 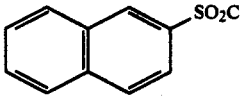 SO$_2$Cl | 2-thionaphthol |
| 12 | 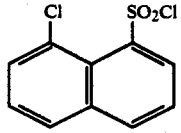 Cl  SO$_2$Cl | 8-chloro-1-thionaphthol |

What is claimed is:

1. A process for the production of an aryl hydrocarbon thiol chloride, which comprises hydrogenating an aryl hydrocarbon sulfonyl in a protic or aprotic solvent in the presence of platinum as catalyst, at a temperature between 100° and 180° C., with hydrogen under a pressure of 2 to 140 bar, in a single pot reaction.

2. A process according to claim 1, wherein sulfidised platinum is used as catalyst.

3. A process according to claims 1 or 2, wherein the hydrogenation is carried out in the temperature range between 120° and 180° C., in particular between 140° and 150° C., and in a hydrogen pressure range between 20 and 120, in particular, between 30 and 100 bar.

4. A process according to claim 3, wherein the catalyst is used on a carrier having a high specific surface area.

5. A process according to claim 4, wherein the carrier is activated charcoal, silica gel, alumina, or magnesia.

6. A process according to claim 1, wherein a lower aliphatic alcohol or dimethyl formamide is used as protic solvent.

7. A process according to claim 6, wherein the alcohol is ethanol, isopropanol or butanol.

8. A process according to claim 7, wherein the alcohol is isopropanol.

9. A process according to claim 1, wherein toluene, a xylene or a chlorobenzene is used as aprotic solvent.

10. A process according to claim 1, wherein the ratio of aryl sulfochloride to solvent is 1:05 to 1:20, in particular 1:2 to 1:5.

11. A process according to claim 1, wherein benzenesulfochloride is used as starting material.

12. A process according to claim 1, wherein 2-naphthalenesulfochloride is used as starting material.

13. A process according to claim 1, wherein 2,5-dichlorobenzenesulfochloride is used as starting material.

* * * * *

UNITED STATES PATENT AND TRADEMARK OFFICE
CERTIFICATE OF CORRECTION

PATENT NO. : 4,209,469
DATED : June 24, 1980
INVENTOR(S) : Hans Thies, et al.

It is certified that error appears in the above-identified patent and that said Letters Patent are hereby corrected as shown below:

Column 1, line 54, "satisfactory" should be --unsatisfactory--.

Signed and Sealed this

Twenty-third Day of September 1980

[SEAL]

Attest:

SIDNEY A. DIAMOND

Attesting Officer

Commissioner of Patents and Trademark